US010698054B2

(12) United States Patent
Leghissa et al.

(10) Patent No.: US 10,698,054 B2
(45) Date of Patent: Jun. 30, 2020

(54) METHOD AND SYSTEM FOR MAGNETIC RESONANCE IMAGING USING SAMPLED PORTIONS OF K-SPACE DATA

(71) Applicant: Siemens Healthcare GmbH, Erlangen (DE)

(72) Inventors: Martino Leghissa, Wiesenthau (DE); Andreas Maier, Erlangen (DE); Bernhard Stimpel, Erlangen (DE); Christopher Syben, Cadolzburg (DE)

(73) Assignee: Siemens Healthcare GmbH, Erlangen (DE)

( * ) Notice: Subject to any disclaimer, the term of this patent is extended or adjusted under 35 U.S.C. 154(b) by 25 days.

(21) Appl. No.: 16/112,139

(22) Filed: Aug. 24, 2018

(65) Prior Publication Data

US 2019/0064292 A1   Feb. 28, 2019

(30) Foreign Application Priority Data

Aug. 25, 2017  (EP) .................................... 17187933

(51) Int. Cl.
*G01R 33/48* (2006.01)
*G06T 11/00* (2006.01)
(Continued)

(52) U.S. Cl.
CPC ....... *G01R 33/482* (2013.01); *G01R 33/4812* (2013.01); *G01R 33/4818* (2013.01); *G01R 33/4822* (2013.01); *G01R 33/4824* (2013.01); *G01R 33/4826* (2013.01); *G01R 33/561* (2013.01); *G01R 33/5608* (2013.01); *G06T 11/006* (2013.01); *A61B 6/027* (2013.01);
(Continued)

(58) Field of Classification Search
USPC .................................................. 324/300–322
See application file for complete search history.

(56) References Cited

U.S. PATENT DOCUMENTS

2011/0286646 A1* 11/2011 Chen ..................... G06T 11/006
                                                                382/131
2012/0146641 A1    6/2012 Wu et al.

FOREIGN PATENT DOCUMENTS

EP            0492897 A2    7/1992

OTHER PUBLICATIONS

Aubry, Jean-François, et al. "Investigation of geometric distortions on magnetic resonance and cone beam computed tomography images used for planning and verification of high—dose rate brachytherapy cervical cancer treatment." Brachytherapy 9.3 (2010): 266-273.

(Continued)

*Primary Examiner* — Jay Patidar
(74) *Attorney, Agent, or Firm* — Lempia Summerfield Katz LLC (57) ABSTRACT

A method and a system for magnetic resonance imaging are provided. The method includes acquiring a magnetic resonance (MR) data set of an object by sampling only a portion of a k-space of the object. This sampled portion may be substantially triangle-shaped or be composed of multiple planes that extend through a point of origin of the k-space and are tangential to a common spherical cap in the k-space. An inverse Fourier transformation is then applied to the MR data set to transform the MR data set from the k-space to image space. A final MR image with a fan- or cone-beam geometry is then computed based on the transformed MR data set in image space.

14 Claims, 4 Drawing Sheets

(51) Int. Cl.
G01R 33/56 (2006.01)
G01R 33/561 (2006.01)
A61B 6/00 (2006.01)
A61B 6/02 (2006.01)

(52) U.S. Cl.
CPC ........... *A61B 6/5247* (2013.01); *G06T 11/005* (2013.01); *G06T 11/008* (2013.01)

(56) References Cited

OTHER PUBLICATIONS

European Search Report for corresponding Application No. 17187933.1-1022, dated Mar. 8, 2018.
Gal, Neville, and Leon Axel. "Characterization of and correction for artifacts in linogram MRI." Magnetic resonance in medicine 3.72 (1997): 275-284.
Napel, Sandy, Shane Dunne, and Brian K. Rutt. "Fast Fourier projection for MR angiography." Magnetic Resonance in Medicine 19.2 (1991): 393-405.

* cited by examiner

METHOD AND SYSTEM FOR MAGNETIC RESONANCE IMAGING USING SAMPLED PORTIONS OF K-SPACE DATA

This application claims the benefit of EP17187933.1, filed on Aug. 25, 2017, which is hereby incorporated by reference in its entirety.

BACKGROUND

The present embodiments relate to magnetic resonance imaging.

The activity leading to this application has received funding from the European Institute of Innovation and Technology (EIT) under grant agreement No EIT/EIT HEALTH/SGA2017/1. This European body receives support from the European Union's Horizon 2020 research and innovation program.

Especially in medical applications, such as stroke therapy, different types of imaging devices and methods, such as X-ray imaging, magnetic resonance (MR) imaging or angiography, may be useful. It is common practice in stroke therapy to use a conventional C-arm X-ray device to acquire several projection images during an intervention to provide a physician with images of, for example, a catheter and a vessel bifurcation. These projection images may be acquired from different angulations (e.g., from different perspectives, projection directions, or viewing angles) depending on an orientation of the vessel bifurcation. An ideal angulation may be determined by extracting the vessel tree using a preliminary 3D digital subtraction angiography (DSA). X-ray images may offer a higher spatial resolution, whereas MR images may offer a better soft tissue contrast.

MR images may be obtained via MR projection acquisition or by sampling a line or plane through the point of origin of k-space and Fourier-transforming the sampled data, which, according to the central slice theorem, results in a projection image. Also, an approach for generating virtual projection MR images with arbitrary angulations from a complete set of k-space data, which does not rely on ray tracing techniques, has been described by Sandy Napel, et al. in "Fast Fourier Projection for MR Angiography," 1991 (https://doi.org/10.1002/mrm.1910190230).

It is, however, problematical that known methods result in MR images based on a parallel beam geometry, while the X-ray projection images are commonly based on a fan- or cone-beam geometry. This provides that X-ray images and MR images are not readily compatible with each other, at least not without further processing.

SUMMARY AND DESCRIPTION

The scope of the present invention is defined solely by the appended claims and is not affected to any degree by the statements within this summary.

The present embodiments may obviate one or more of the drawbacks or limitations in the related art. For example, an improved medical imaging technique is enabled using MR imaging.

A method according to one or more of the present embodiments is concerned with magnetic resonance (MR) imaging. The method includes acquiring an MR data set of a first portion of an object by sampling only a portion of a k-space of the object. The sampled portion of the k-space may be substantially formed like one triangle or cone, or like two symmetrically arranged triangles or cones. A respective tip of each triangle or cone is located at the point of origin of a coordinate system of the k-space, and each triangle or cone extends along an ordinate axis of the coordinate system. A point of origin of the coordinate system may also be denoted as the point of origin of the k-space. The sampled portion of the k-space may equally be composed of multiple planes, where each plane extends from or through the point of origin and is tangential to a common sphere or spherical cap in k-space. This provides that all planes are tangential to the same sphere or spherical cap. The sphere or spherical cap may be centered around or symmetrically arranged around the ordinate axis. In a following act of the method, an inverse Fourier transformation is applied to the MR data set to transform the MR data set from k-space to image space. Another act of the method includes computing a final MR image or projection with a fan- or cone-beam geometry based on the transformed MR data set in image space. The sampled portion of the k-space may be formed or shaped like the above-mentioned one or two triangles for the case of a fan-beam geometry. This case may correspond to the 1D/3D-version of the Fourier central slice theorem. The sampled portion of the k-space may include or be composed of the above-mentioned planes or parts thereof for the case of the cone-beam geometry. This case may correspond to the 2D/3D-version of the Fourier central slice theorem. Correspondingly, the final MR image may be a 2D-image or a 3D-image.

For example, for medical applications, the object may be a patient, a part of a patient, or a tissue sample. It may, however, be possible to apply the one or more of the present embodiments in other technical fields or industries (e.g., to image technical devices or component parts).

In a development, X-ray image data of a second portion of the object is acquired using a fan- or cone-beam geometry as part of the method according to one or more of the present embodiments in an additional process act. Therein, the first portion and the second portion at least partly overlap each other. The final MR image is then computed with a fan- or cone-beam geometry corresponding to the fan- or cone-beam geometry of the X-ray image data. At least in this development, the method according to one or more of the present embodiments becomes a method for combined radiography and magnetic resonance imaging. The first portion and second portion at least partly overlapping each other provides that a part of the object where both portions overlap is imaged or pictured by X-ray imaging as well as by MR imaging. Using a fan- or cone-beam geometry for acquiring the X-ray image data provides that the X-ray radiation used to acquire or to generate the X-ray image data has a certain angle of beam and originates at what is substantially a point source. The individual rays of the X-ray radiation therefore are not parallel to each other but rather form a fan-shape for 2D imaging or a cone-shape for 3D imaging. Different beam geometries, such as fan-beam, cone-beam, or parallel beam may radiograph different parts of the object and may result in different images or in images with different characteristics or properties, such as a specific or characteristic distortions depending on the beam geometry. For 2D imaging, a fan-beam geometry may be used for acquiring the X-ray image data, and correspondingly, the final MR image is computed to have a fan-beam geometry. For 3D imaging, a cone-beam geometry may be used for acquiring the X-ray image data, and correspondingly, the final MR image is then computed to have a cone-beam geometry. For the final MR image to have a certain geometry provides that the final MR image has the corresponding characteristics or properties corresponding to or specific to a projection image created or obtained by using a real or virtual beam of the corresponding beam geometry.

The required MR data set, which may be obtained and provided by an MR imaging device, consists of data points in k-space. In terms of the present embodiments, k-space refers to the corresponding formalism widely used in magnetic resonance imaging, which should be well-known to those skilled in the art. K-space may be an array, a grid, or a matrix that gets filled or populated with measured values taken directly from an MR signal of the MR imaging device. These measured values represent spatial frequencies, providing that the object or at least the imaged second portion of the object is or may be represented as spatial frequencies in k-space. K-space, therefore, is a spatial frequency domain, and the Fourier-formalism may be used to transform between position or image space and k-space. K-space may be spanned by the coordinate system with the ordinate axis representing spatial frequencies of the MR image in a Y-direction and an abscissa of the coordinate system representing spatial frequencies in an X-direction. Each data point in k-space contains special frequency and phase information about every pixel in the final image.

The central slice theorem states that the inverse Fourier transform of a line or plane through the point of origin of the k-space is equivalent to a parallel beam projection onto a detector (e.g., a projection line or projection plane that is parallel to the line or plane, respectively). The present embodiments are based on the insight that the conventional central slice may be adapted. The Fourier transform of a fan-beam projection is a triangle or wedge or hourglass-shape in the Fourier- or k-space. The data or information of a cone-beam projection is correspondingly contained in a portion or shape in the Fourier- or k-space composed of planes through the point of origin and fanned out or angled with respect to each other so that all of the planes are tangential to the same sphere or spherical cap. The planes may be described as being tilted and/or rotated about the point of origin.

By sampling only the described portion of the k-space, exactly those data or data points that are needed to generate the final MR image having the corresponding fan- or cone-beam geometry may be acquired. The Fourier space is point symmetric. This point symmetry may be exploited by, for example, sampling only MR data points from or in a positive half or half-plane of the k-space, or from or in a negative half or half-plane of the k-space. Whether or not this approach is used may, for example, depend on a respective sampling trajectory used to acquire the respective MR data set (e.g., the MR data points or sampling points) on a case-by-case basis.

Applying the inverse Fourier transformation to the MR data set results in or generates at least one parallel projection MR image (e.g., an MR image having a parallel beam geometry or distortion characteristics corresponding to a parallel beam projection). Depending on a sampling scheme or sampling trajectory (e.g., a path or pattern used to acquire the individual data points of the MR data set), MR data points corresponding to or belonging to one line or plane in k-space may be inversely Fourier transformed together as a group or chunk of data. This provides that multiple inverse Fourier transformations may be performed on the MR data set, with each inverse Fourier transformation being applied to only a part of the complete MR data set until, at least substantially, the complete MR data set has been inversely Fourier transformed. Each inverse Fourier transformation then generates an individual parallel projection MR image.

From the transformed MR data set (e.g., the at least one parallel beam projection or parallel projection MR image or the multiple parallel projection MR images or a stack of these multiple parallel projection MR images), the final MR image may be computed or generated.

In case the final MR image is to have a fan-beam geometry, the portion of the k-space may be sampled along lines through the point of origin of the k-space. In case the final MR image is to have a cone-beam geometry, the portion of the k-space may be sampled along the above-mentioned planes. Each line or plane, or the corresponding MR data, may be individually inversely Fourier transformed. Each of these individual inverse Fourier transformations results in a parallel-beam projection (e.g., an MR image having a parallel-beam geometry). Inversely Fourier transforming the complete MR data set may therefore result in multiple parallel-beam projections (e.g., the above-mentioned stack of multiple parallel projection MR images). From these multiple projections or projection images, integral-values (e.g., line-integral values) may be taken or chosen as needed to construct a fan- or cone-beam projection (e.g., the final MR image). The data or values of the multiple projections get, in other words, rebinned to generate the final MR image. This process of generating or creating the final MR image having a fan- or cone-beam projection from the data or values of the parallel-beam projections may therefore be denoted as rebinning of the transformed MR data set. Since the final MR image having a fan- or cone-beam geometry is generated or computed without doing an actual fan- or cone-beam projection, the process may also be denoted as a virtual fan- or cone-beam projection, because the resulting MR image has the same geometry or characteristics as a fan- or cone-beam projection image, such as a typical X-ray image. Because the MR data set does only contain data from a sub-portion of k-space, computing the final MR image from the transformed MR data set may be relatively computationally inexpensive (e.g., as compared to conventional methods).

The method according to one or more of the present embodiments may be used to automatically generate MR images corresponding to or having the same projection geometry as typical or commonly used X-ray images, thereby creating final MR images that are compatible (e.g., directly comparable to the X-ray images), since the final MR images have the same distortion or projection characteristics (e.g., the same geometry). For example, these MR images may be generated using only a subset of the full MR data set that is typically acquired by sampling the complete k-space of the respective object in conventional methods.

Since the MR data set acquired using the presently described method only and exactly contains the subset of the complete k-space data of the object needed for or corresponding to the final fan- or cone-beam geometry MR image, there is no need for a complex data selection step. Also, by sampling only the limited portion of the k-space needed for the final MR image, acquisition of the MR data set as well as the necessary processing steps, such as the inverse Fourier transformation, may be performed significantly faster as compared to traditional methods, where the complete k-space of the object is sampled and therefore a much larger MR data set is to be processed. The present embodiments therefore enable substantially real-time acquisition, processing, and displaying of MR images that are directly comparable and compatible to standard X-ray images. Since the final MR image and an X-ray image reconstructed from the acquired X-ray image data may have or correspond to the same beam or projection geometry, this obviates the need for a complex and time-consuming registration step that is necessary in conventional methods for correlating the X-ray and MR images. Not only do the present embodiments enable a direct superposition of the X-ray and MR images, but the present embodiments do so with reduced data acquisition effort, reduced computational effort, and reduced processing time.

To speed up the data acquisition and/or data processing time even further, the present embodiments may be combined with acceleration techniques, such as compressed sensing. With or without the use of additional acceleration techniques, the present embodiments may meet the time constraints or time requirements posed by interventional applications or an interventional environment.

In a development, the portion of the k-space is sampled along lines if the portion of the k-space is formed like the one or two triangles. These lines or sampling lines extend from or through the point of origin of the k-space. The inverse Fourier transformation is then applied separately or individually to respective data for or of each line or plane, thereby generating an interim MR image with a parallel projection geometry for each line or plane. This provides that, as described, a stack of interim MR images is generated. The final MR image may then be computed based on multiple (e.g., all) of these interim MR images by rebinning data of the interim MR images.

The multiple lines or planes may be arranged equidistantly or with the same angle enclosed by any two neighboring lines or planes, which may provide consistent and uniform detail across the sampled portion of the k-space. Sampling the portion of the k-space along lines or planes may be achieved using a sampling scheme or sampling trajectory that matches or corresponds to the shape of the sampled portion particularly well with minimal programming effort or effort in terms of necessary movements or adjustments of the MR imaging device, since a bundle of lines or planes all extending through the same point of origin and angled with respect to each other may naturally or automatically form or span a triangle, wedge, or a substantially hourglass-shaped form. Sampling the portion of the k-space in this manner may be described as using a radial sampling scheme, since the lines of sampling points may extend regularly outwards from the point of origin. Sampling points or data points of multiple lines may be arranged on concentric circular arcs around the point of origin, where each arc spans or crosses multiple lines. The outermost sampling lines may coincide with the outer edges or limits of the portion of the k-space to be sampled.

In another development, the portion of the k-space is sampled using a Cartesian grid sampling scheme or a sampling scheme with sampling points arranged on two lines crossing the portion of the k-space from one edge to the other in opposing zigzag schemes. In the Cartesian sampling scheme, the sampling points (e.g., the points of or in k-space where MR data is measured or collected) may, for example, be located or arranged at intersections of a grid of orthogonal lines overlaid or superimposed on the k-space or the portion of the k-space to be sampled. Even though the sampling points of this Cartesian sampling scheme may not necessarily provide the best match or fit for the form or shape of the portion of the k-space to be sampled, the Cartesian sampling scheme may be advantageous to use, since the Cartesian sampling scheme may be extremely easy and reliable to implement and/or may facilitate the use or application of a Fast Fourier transform algorithm to transform the MR data set form k-space to image space, further reducing processing time.

Using the zigzag sampling scheme may allow for sampling the portion of the k-space without diminishing density of sampling points with increasing distance from the point of origin with respect to the area of the sampled portion of k-space, which may result in an improved image quality or level of detail in the final MR image.

Regardless of the used sampling scheme, the sampling points may be arranged equidistantly spaced along or across the respective lines or planes to simplify the data acquisition and to limit the amount of data and correspondingly the necessary processing time. Depending on the used sampling scheme, it may, however, be advantageous to reduce the distance between two neighboring sampling points along the lines or planes with increasing distance from the point of origin to limit or counteract the effect of decreasing density of sampling points with increasing distance from the point of origin that may otherwise occur. Other sampling schemes or sampling trajectories may also be used and may provide improved results depending on specific requirements or conditions of a respective application or use case.

In general, the sampling scheme or sampling trajectory to be used for sampling the portion of the k-space may be selected depending on time constraints for the data acquisition and/or data processing, depending on occurring artifacts in the resulting final MR image or MR images, and/or depending on the resulting image quality of the final MR image or MR images. The sampling scheme may be selected manually before acquiring the MR data set. It may, however, also be possible to automatically select the sampling scheme, for example, depending on a respective procedure to be performed, depending on a specified parameter, depending on a size of the portion of the k-space to be sampled, depending on whether or not additional acceleration techniques, such as compressed sensing, are used, and/or depending on other factors.

In a development, the final MR image is generated using the same angle and/or orientation for the corresponding fan- or cone-beam geometry as is being used or as has been used in acquiring the X-ray image data. If, for example, the final MR image is generated by a virtual fan- or cone-beam projection, then corresponding parameter values, such as a viewpoint or source and an angle of beam, are the same for both the virtual projection and the actual X-ray image data acquisition. This provides that the X-ray image data or an X-ray image reconstructed therefrom and the final MR image may be superimposed or overlaid upon each other without any further data processing, registration, or adaptation. Thus, a combined image or display may be generated or provided showing, for example, a catheter, medical wires, and surrounding soft tissue with the respective advantages of X-ray imaging and MR imaging techniques, at least substantially, in real-time. This is an advantage over existing methods and may advantageously provide a respective physician with a more detailed context and a more comprehensive understanding of the respective medical situation. The present embodiments may therefore lead to improved diagnostic and/or interventional results. Using the same angle and/or orientation (e.g., the same geometry) for both the final MR image and the X-ray image provides that corresponding real or virtual projection beams for the final MR image and the X-ray image completely overlap each other, so that the MR data set and the X-ray image data picture the same parts of the object. In this case, the first portion and the second portion of the object are therefore identical.

In another development, the final MR image is generated using a different angle and/or orientation for the corresponding fan- or cone-beam geometry than for acquiring the X-ray image data. If, for example, the final MR image is generated using a virtual fan- or cone-beam projection, then the corresponding virtual fan- or cone-beam may be tilted with respect to the fan or cone of the X-ray-beam used to acquire the X-ray image data. The final MR image and the X-ray image data or an X-ray image reconstructed therefrom may in this case therefore show different parts of the object and/or to a specific part of the object from different angulations (e.g., angles or viewing angles or viewpoints). This approach may, in other words, provide different perspectives of the object, which may provide a respective physician with an improved spatial understanding of the respective medical situation.

Even though the resulting final MR image and X-ray image may not necessarily be readily superimposed upon each other, since the resulting final MR image and X-ray image may differ in terms of field of view or perspective, it may be advantageous for both the final MR image and the X-ray image to have the same characteristics corresponding to a fan- or cone-beam projection geometry. This may allow for an easy and meaningful direct comparison, since, for example, both images may have the same scale and/or geometry or perspective distortion. Imaging, for example, a vascular bifurcations with or from different angulations may help the physician to visualize the three-dimensional structure of the corresponding vessel and may therefore enable an exact and safe navigation of a medical tool or device, such as a catheter.

Having different perspectives or viewing angles for the final MR image and the X-ray image may also be advantageous if, for example, an ideal angulation may not be reached with the X-ray imaging device. Since generating the final MR image with a fan- or cone-beam projection geometry includes only a virtual or mathematical projection, the direction of which may be arbitrarily chosen, the present embodiments may provide needed or useful visualization in an especially constrained situation or scenario.

In a development, an interpolation of the MR data set in k-space is performed to generate interpolated data points in k-space. The inverse Fourier transformation is then applied to the interpolated data points. Alternatively or additionally, an interpolation of the Fourier transform of the MR data set is performed to generate interpolated data points in image space, and the final MR image is then generated based on these interpolated data points in image space. By computing the interpolated data points, the MR data set may be adapted to a shape of the sampled portion of k-space, so that no data corresponding to points in k-space outside the portion to be sampled is used or processed in steps following the interpolation, which may improve computational efficiency. The interpolation may also be used to align pixels or pixel locations of the final MR image with a predetermined standard or, for example, with the pixels or pixel locations of the X-ray image data. The interpolation may also be used to compute interpolated data points that are arranged on a Cartesian grid even if the data points of the MR data set do not correspond to or align with such a grid. Having data points in k-space arranged on a Cartesian grid may enable the use of a fast Fourier transformation technique for transforming the MR data from k-space to image space, which may shorten the necessary processing time needed for generating the final MR image.

In a development, the X-ray image data and the MR data set are acquired substantially simultaneously (e.g., within 200 ms of each other). A simultaneous acquisition in this sense refers to a human timescale or a timescale of human perception, providing that the acquisition takes place simultaneously for practical purposes but may actually be performed sequentially on a timescale of an execution of individual commands by an electronic processing unit. Depending on a system used to perform the method described herein, it may, however, be possible to acquire the X-ray image data and the MR data set precisely simultaneously.

The present embodiments enable this at least substantially simultaneous acquisition by limiting the area or volume of k-space that is sampled for generating the final MR image. By contrast, traditional methods that acquire MR data for the complete k-space of the object may result in significantly longer acquisition times for the respective MR data set than for the X-ray image data, which provides that traditionally even X-ray image data and a corresponding MR data set of the same portion of the object do not necessarily show the object in the same state or at the same point in time. By acquiring the X-ray image data and the MR data set substantially simultaneously, the present embodiments may provide that the X-ray image data or the X-ray image reconstructed therefrom and the final MR image may be used or evaluated together (e.g., superimposed on each other in real time), since the X-ray image data or the X-ray image reconstructed therefrom and the final MR image may show the same portion of the object at at least substantially the same point in time or in the same state and with the same projection geometry.

In a further development, the X-ray image data or an X-ray image reconstructed therefrom, and the final MR image are automatically superimposed or overlaid upon each other. This provides that effectively a single combined image or display of all collected or generated image data may automatically be generated. The X-ray image data or X-ray image and the final MR image may, in other words, be combined into a single dataset or image and/or may be displayed superimposed upon each other (e.g., on a medical monitor or display device) in, for example, real time. This may enable the respective physician to benefit from the different characteristics of X-ray images and MR images without any manual control actions or operational actions, which may improve a safety and an outcome of the respective medical procedure. The X-ray image data and the MR data set may not only be acquired substantially simultaneously but may also be automatically displayed substantially in real-time after acquiring the respective data (e.g., within less than one second of the respective data acquisition). This is also enabled by reducing the amount of data collected or measured for the MR data set due to the corresponding reduction in acquisition time as well as in processing time.

Another aspect is a system for magnetic resonance imaging. The system includes a magnetic resonance imaging device (MR device) for acquiring an MR data set of a first portion of an object by sampling only a portion of the k-space of the object. Therein, the sampled portion of the k-space may be substantially formed like one triangle or cone, or like two symmetrically arranged triangles or cones, with a respective tip of each triangle or cone located at the point of origin of a coordinate system of the k-space, or the point of origin of the k-space itself. Each triangle or cone extends along an ordinate axis of the coordinate system of the k-space. The sampled portion of the k-space may equally be composed of multiple planes, where each plane extends through the point of origin and is tangential to a common spherical cap in k-space. The system further includes a data processing device for automatically applying an inverse Fourier transformation to the MR data set to transform the MR data set from k-space to image space. The data processing device is configured for automatically computing a final MR image with a fan- or cone-beam geometry based on the transformed MR data set in image space.

In a development of the system, the system further includes an X-ray device for acquiring X-ray image data of a second portion of the object using a fan- or cone-beam geometry. Therein, the second portion partly or fully overlaps the first portion. The data processing device is then further configured to automatically compute the final MR image to have a fan- or cone-beam geometry corresponding or equal to the fan- or cone-beam geometry of the X-ray image data. This system according to one or more of the present embodiments, which may be or denoted as a multi modal MR/X-ray device or MR-Angiography hybrid device, may be used to acquire X-ray image data and corresponding MR data of the same portion or region of the object substantially simultaneously.

In a development of the system, the X-ray device and the magnetic resonance imaging device are arranged so that the isocenters of both devices spatially coincide. Arranging the X-ray device and the magnetic resonance imaging device with spatially coinciding isocenters provides that the isocenter of the X-ray device is located at the same point in space as the isocenter of the magnetic resonance imaging device. Depending on the devices, the same may be true if the respective isocenters are or extend along lines, planes, or volumes. Arranging the X-ray device and the MR device with spatially coinciding isocenters may enable or simplify simultaneous acquisition of respective data corresponding to the same portion of the object. Arranging the X-ray device and the MR device with spatially coinciding isocenters may also limit a movement or adjustment necessary for the respective data acquisition, which may shorten an overall process time or acquisition time and/or reduce wear on the system.

In a development of the system, a magnet of the MR device, which creates a magnetic field for the magnetic resonance imaging process, is movably mounted, so that the magnet may be tilted with respect to the X-ray device or X-ray imaging device. This may improve a range of angulations accessible for imaging or data acquisition to the X-ray device and/or the MR device. If, for example, a head of a patient is to be examined, but the X-ray device may not be set to a cranial-caudal angulation due to limitations in the range of motion of the system or the X-ray device, the magnet of the MR device may be tilted to capture or measure the corresponding MR data used for creating or generating the final MR image with a perspective corresponding to the desired cranial-caudal angulation. Additionally or alternatively, the magnet of the MR device may be tilted out of the way of the X-ray device to allow for a greater range of motion of the X-ray device. For example, the magnet of the MR device may be tiltable by at least 10° in each direction or in two opposing directions.

The system according to one or more of the present embodiments may include one or more control elements and/or interfaces to enable an operator to selectively operate or control the X-ray device and the MR device. The system may include a control element or interface for a combined operation or control of the X-ray device and the MR device. For example, the system may include a first control element for triggering the acquisition of only the X-ray image data, a second control element for triggering the acquisition of only the MR data set, and a third control element for triggering the simultaneous acquisition of both the X-ray image data and the MR data set.

The data processing device may include one or more computer- or microchips configured to execute a program code representing or encoding commands or instructions in accordance with a method according to one or more of the present embodiments. The system may, in other words, be configured to execute or perform at least one embodiment of the method. The respective program code may, for example, be contained in a storage medium that may be part of the data processing device and/or the system according to the present embodiments. The storage medium containing the program code representing or encoding at least one embodiment of the method may be another aspect of the present embodiments.

The embodiments and developments described herein for at least one aspect (e.g., for the method, the system, and/or the storage medium), as well as the corresponding advantages may be applied to any and all aspects.

BRIEF DESCRIPTION OF THE DRAWINGS

The features and feature combinations previously mentioned in the description as well as the features and feature combinations mentioned in the following description of the figures and/or shown in the figures alone may be employed not only in the respectively indicated combination but also in other combinations or taken alone without leaving the scope of the present invention.

DETAILED DESCRIPTION

Figure 1:
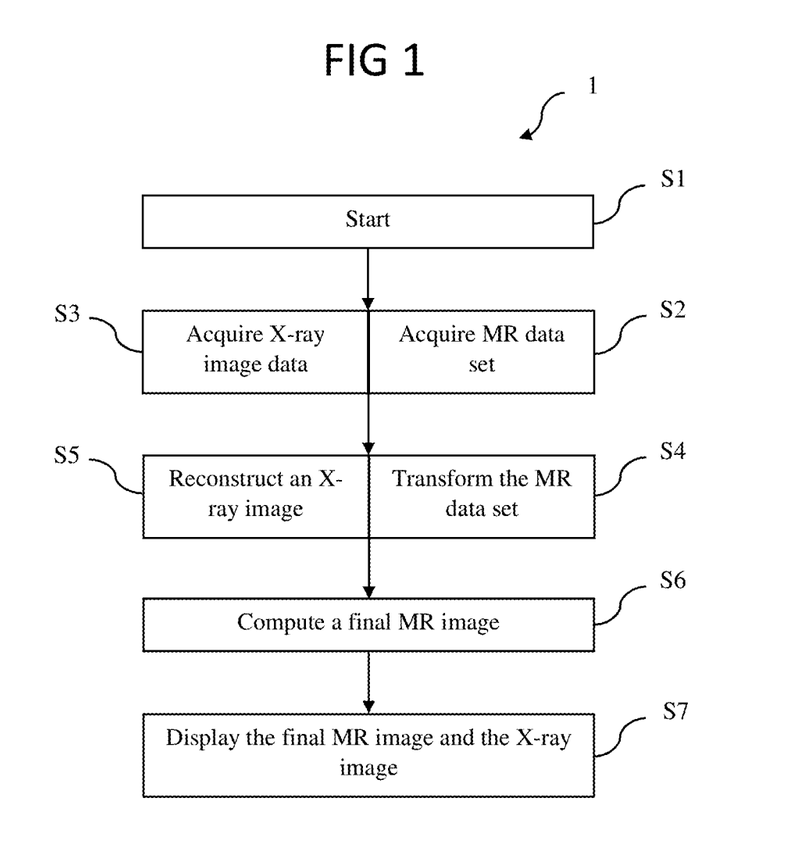
FIG. 1 schematically shows an exemplary flow chart illustrating a method for combined radiography and magnetic resonance imaging.

FIG. 1 schematically shows an exemplary flow chart 1 illustrating a method for combined radiography and magnetic resonance imaging. In a first process act S1, the method is started. A system used to carry out the method may be activated or set up, an object or a portion of the object to be imaged may be specified, and this specification as well as any other settings or parameters and/or control actions (e.g., for triggering the execution of the method) may be detected and/or processed. The system used to carry out the method may include an X-ray device for acquiring X-ray image data of the object in a fan- or cone-beam geometry, providing that a resulting X-ray image is a projection image generated by X-raying or radiographing the object with X-rays from a point source and detecting the X-ray radiation transmitted through the object (e.g., using an X-ray detector extending in two dimensions). The system may further include a magnetic resonance (MR) imaging device for acquiring an MR data set of the object by sampling a portion of the k-space of the object. Additionally, the system may include a data processing device for processing the acquired X-ray image data and the acquired MR data set to generate an X-ray image from the X-ray image data and a final MR image from the MR data set.

For example, the system is configured to generate the final MR image so that the final MR image has the same projection geometry (e.g., the same fan- or cone-beam geometry or corresponding geometric distortion) as the X-ray image or the X-ray image data. For this purpose, the MR data set is acquired in a process act S2 by sampling only a portion of the k-space of the object, where this sampled portion of the k-space is substantially formed or shaped like one triangle or cone or like two symmetrically arranged triangles or cones. A respective tip of each triangle or cone is located at the point of origin of a coordinate system of the k-space, and each triangle or cone extends along an ordinate axis of the coordinate system. This approach is based on the insight that a Fourier transform of a fan- or cone-beam projection is or may be represented as just such a form or shape in Fourier space (e.g., in k-space). An example of this form or shape of the sampled portion is illustrated in FIGS. 2 to 5.

Figure 2:
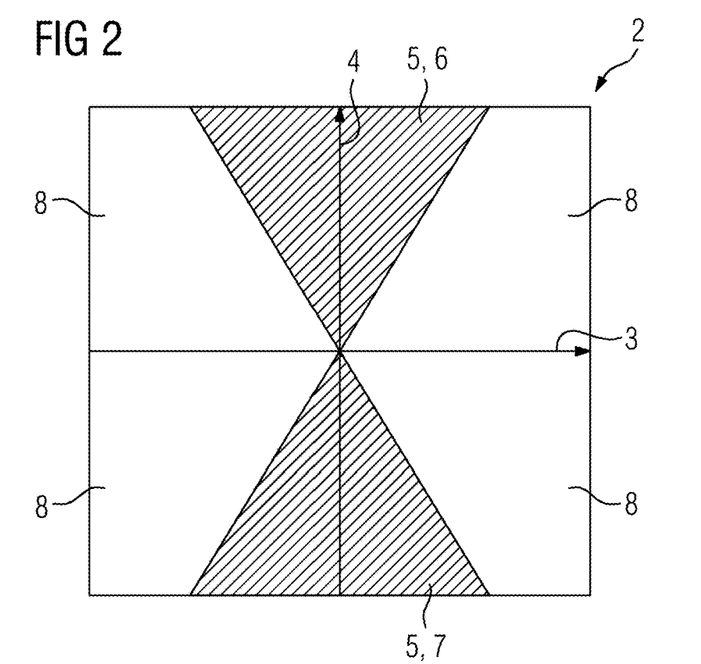
FIG. 2 schematically illustrates k-space with a portion to be sampled for generating a final MR image with a fan-beam geometry.

FIG. 2 schematically illustrates the sampled portion of the k-space. FIG. 2 shows a first diagram 2 representing the two-dimensional k-space. In the first diagram 2, X-axis 3 represents spatial frequencies in a first direction, and a Y-axis 4 represents spatial frequencies in a second direction. Illustrated in the coordinate system spanned by the X-axis 3 and the Y-axis 4 is the sampled portion 5, which represents the measured or acquired MR data set. Since a resolution of any real MR imaging device is limited, the sampled portion 5 is sampled, providing that only a finite number of data points are measured or recorded to represent the sampled portion 5. The sampled portion 5 includes an upper triangle 6 arranged with a tip located at a point of origin of the k-space and symmetrically extending along the positive Y-axis 4. The sampled portion 5 also includes a lower triangle 7 that extends from the point of origin along the negative Y-axis 4 symmetrically to the upper triangle 6. In contrast to traditional methods, a remainder 8 of the k-space is not sampled, resulting in shorter sampling times and therefore a faster acquisition of the MR data set. Sampling only the sampled portion 5 is, however, sufficient, since the sampled portion 5 contains all data necessary to generate the final MR image with the desired fan- or cone-beam geometry.

In a process act S3, the X-ray image data is acquired. The process acts S2 and S3 may be carried out substantially simultaneously.

In a process act S4, the data processing device may apply an inverse Fourier transformation to the acquired MR data set, transforming the MR data set from k-space to image space. For example, the MR data set may be split up into portions, chunks, or groups of sampling points or data points, with each group arranged on a line or plane through the point of origin of the k-space. Each such portion may then individually be inversely Fourier transformed to generate a stack of multiple parallel projections or parallel projection images (e.g., interim MR images with a parallel projection geometry).

In a process act S5, the data processing device may reconstruct an X-ray image from the X-ray image data acquired in process act S3. In one embodiment, the process acts S4 and S5 may be carried out substantially simultaneously, at least on a human timescale or a timescale of human perception.

In a process act S6, the final MR image having a fan- or cone-beam geometry corresponding to the fan- or cone-beam geometry of the X-ray image is computed from the transformed MR data set in image space (e.g., from the stack of parallel projection images). Computing the final MR image may include a virtual fan- or cone-beam projection and/or a rebinning of the data or data points of the transformed MR data set. The process act S4 and/or the process act S6 may also include an interpolation of the measured values and/or of the transformed data points or values, respectively, generating respective interpolated data points. These interpolated data points may then be used instead for the respective following processing acts.

In a process act S7, the final MR image as well as the X-ray image may be automatically displayed on a display device. This act may advantageously occur substantially in real time (e.g., within 1 second of the process acts S2 and S3). If the final MR image and the X-ray image show the object from the same angulation or perspective, the final MR image and the X-ray image may be overlaid or superimposed upon each other to generate and/or display a combined image showing details of both the final MR image and the X-ray image.

Figure 3:
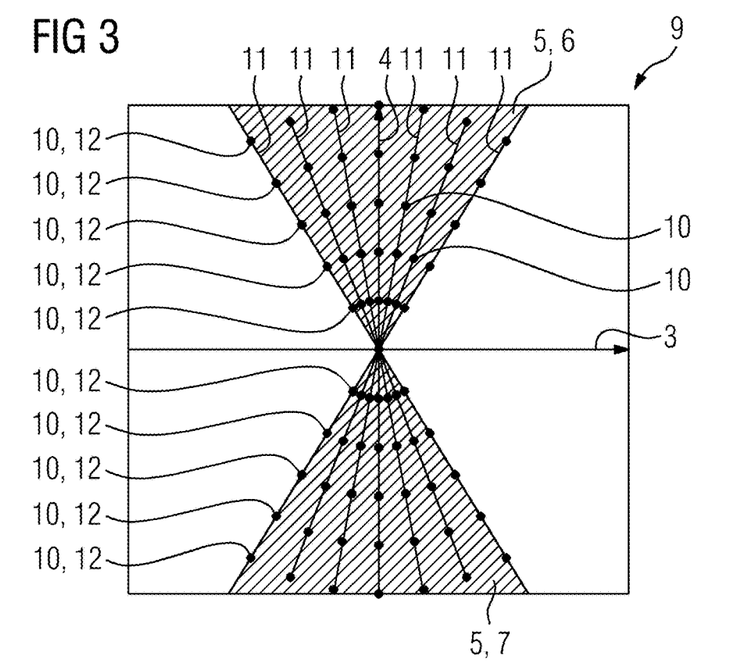
FIG. 3 schematically illustrates a radial sampling scheme for the portion of k-space.

To acquire the data necessary for creating or generating the final MR image or for the virtual fan- or cone-beam projection resulting in the final MR image, different sampling schemes may be employed for sampling the upper triangle 6 and the lower triangle 7, and/or the MR data set. FIG. 3 shows a second diagram 9 with the same coordinate system and sampled portion 5 as the first diagram 2. Illustrated in the second diagram 9 is a radial sampling scheme for sampling the sampled portion 5. Using this radial sampling scheme, the portion 5 is sampled at radial sampling points 10 that are arranged along multiple radial sampling lines 11 extending through the upper triangle 6, the lower triangle 7, and the centrally arranged point of origin of the k-space or the coordinate system spanned by the X-axis 3 and the Y-axis 4. As a result, the corresponding radial sampling points 10 of multiple radial sampling blinds 11 are arranged on multiple concentric circular arcs 12, which span the upper and lower triangles 5, 6. In FIG. 3, only some of the sampling points 10 are indicated for improved visual clarity of the drawing.

Figure 4:
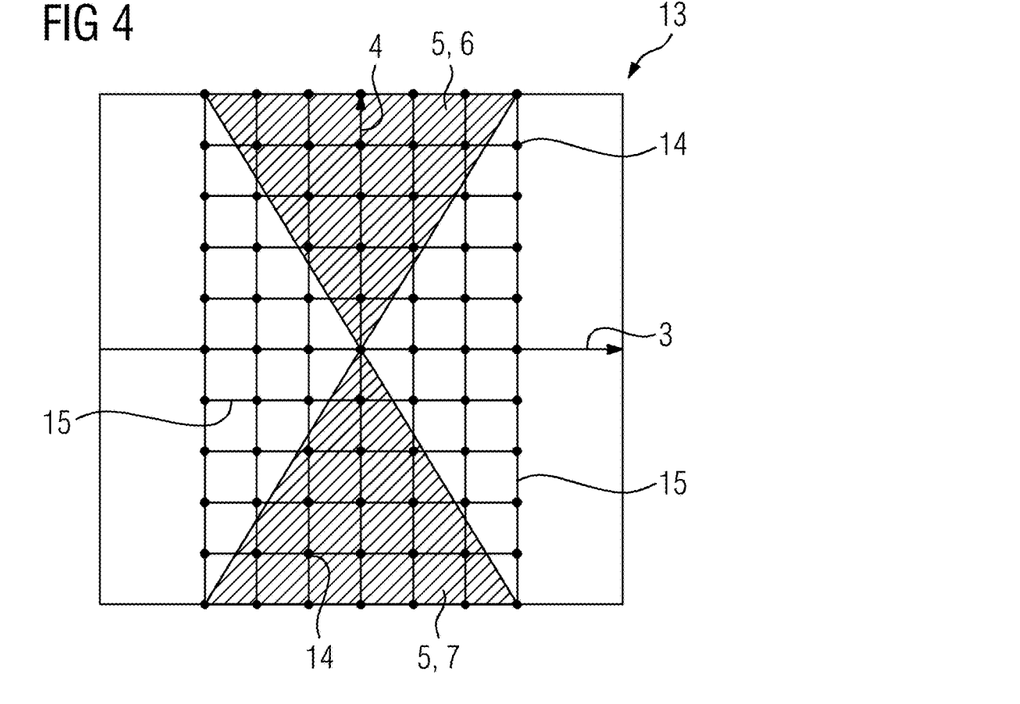
FIG. 4 schematically illustrates a Cartesian sampling scheme for the portion of k-space.

FIG. 4 shows a third diagram 13 including the same coordinate system of k-space and the same sampled portion 5 as illustrated in FIG. 2 and FIG. 3. FIG. 4 schematically illustrates a Cartesian sampling scheme for the sampled portion 5. Cartesian sampling points 14 are arranged regularly on intersections of a Cartesian grid 15, which consists of multiple lines parallel to the X-axis 3 and multiple lines parallel to the Y-axis 4. While this may enable the use of a fast Fourier transformation technique for transforming the MR data set from k-space to image space, the Cartesian sampling scheme would acquire more data than necessary (e.g., the Cartesian sampling scheme) would acquire data for data points outside the upper and lower triangle is 6, 7. Only some of the Cartesian sampling points 14 and only some of the lines of the Cartesian grid 15 are indicated.

Figure 5:
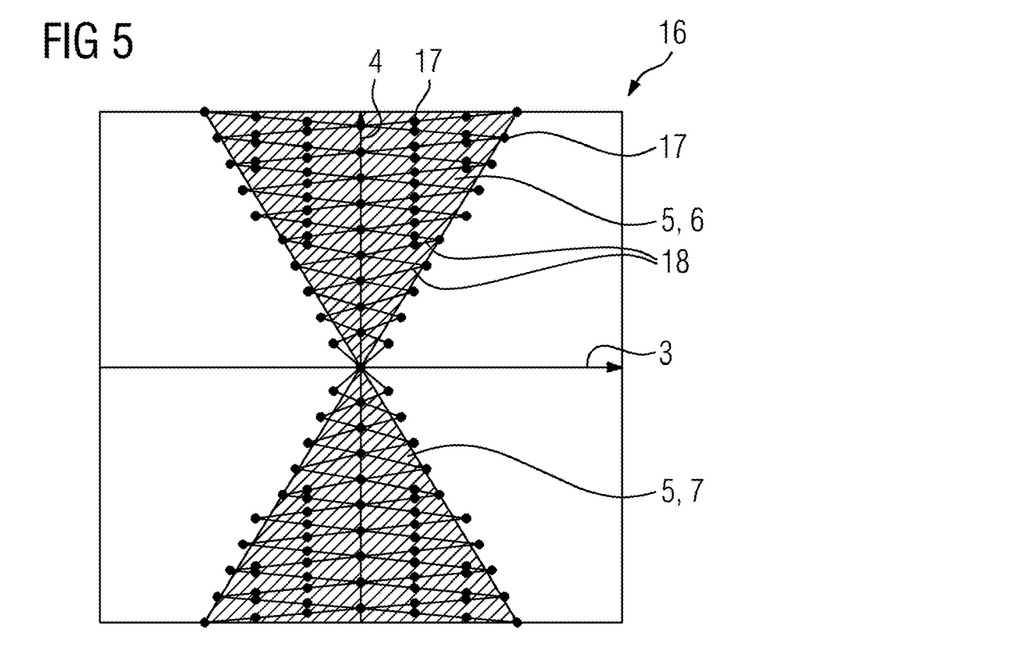
FIG. 5 schematically illustrates a zig-zag sampling scheme for the portion of k-space.

FIG. 5 shows a fourth diagram 16 that also includes the same coordinate system and illustration of the sampled portion 5 as is shown in FIG. 2, FIG. 3, and FIG. 4. Schematically illustrated in FIG. 5 is a zigzag sampling scheme, where the zigzag sampling points 17 are arranged along two zigzag sampling lines 18 crossing the upper and lower triangles 5, 6 back and forth from side to side. The zigzag sampling lines 18 may cross the Y-axis 4 at opposite angles. While the zigzag sampling points 17 may be arranged equidistantly (e.g., at constant spatial intervals along the zigzag sampling lines 18), just as may be the case with the radial sampling scheme illustrated in FIG. 3, the zigzag sampling scheme advantageously avoids a diminishing density of sampling points with increasing distance from the point of origin with respect to an area of the sampled portion 5. For better visibility, only some exemplary zigzag sampling points 17 are indicated.

Figure 6:
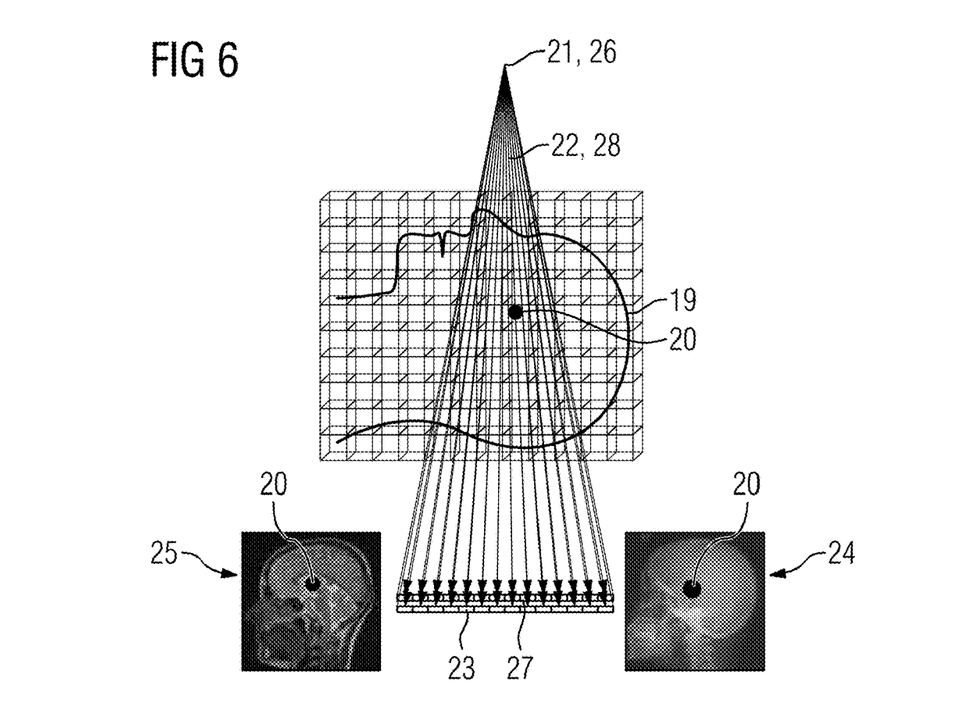
FIG. 6 schematically illustrates an acquisition geometry of X-ray image data and a corresponding geometry of a virtual projection used for generating a final MR image having the same angulation as the X-ray image.
Figure 7:
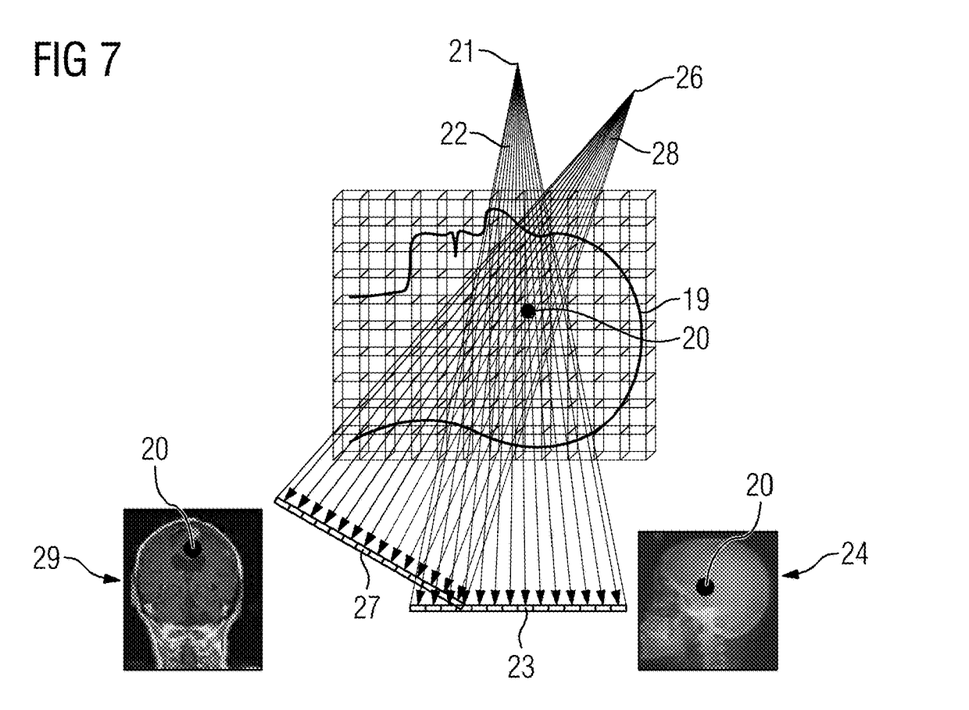
FIG. 7 schematically illustrates an acquisition geometry of X-ray image data and a corresponding geometry of a virtual projection used for generating a final MR image with a different angulation.

FIG. 6 and FIG. 7 each schematically illustrate an acquisition geometry of X-ray image data and a corresponding geometry of a virtual projection applied to the transformed MR data set. In both cases, a medical detail of a patient 19, such as, for example, a tumor 20 located inside the patient's head, is to be imaged using X-ray imaging as well as MR imaging. In both cases, X-ray radiation is emitted from an X-ray point source 21 in a fan- or cone-beam 22 and captured or detected using an X-ray detector 23. A resulting X-ray image 24 is also schematically shown.

In the case shown in FIG. 6, a first final MR image 25 is generated or computed through the virtual fan- or cone-beam projection corresponding to the projection geometry used for generating the X-ray image 24. This provides that the MR data set is processed so that the resulting first final MR image 25 has the same geometric characteristics or distortion characteristics as the X-ray image 24 and may therefore be directly superimposed upon the X-ray image 24 to combine all available image information into a single combined image or display. For this purpose, the virtual projection of the transformed MR data from a virtual point source 26 to a virtual detector 27 using a virtual fan- or cone-beam 28 may be performed. In this case, the virtual point source 26 spatially coincides with the X-ray point source 21, and the virtual detector 27 aligns with the X-ray detector 23. This provides that the X-ray fan- or cone-beam 22 and the virtual fan- or cone-beam 28 completely overlap each other, so that the X-ray image 24 and the first final MR image 25 are directly and readily compatible and may be overlaid or superimposed upon each other without any further processing or registration acts.

In the case shown in FIG. 7, however, the virtual point source 26 does not spatially coincide with the X-ray point source 21, and correspondingly, the virtual detector 27 does not spatially coincide or align with the X-ray detector 23. This provides that the virtual fan- or cone-beam 28 is tilted with respect to the X-ray fan- or cone-beam 22. This provides that the virtual projection applied to the transformed MR data set is performed using a different angulation, so that a resulting second final MR image 29 shows the object (e.g., the patient 19 or the tumor 20) from a different perspective than the X-ray image 24. It may however, be advantageous to use the same angle of beam for the virtual projection and the X-ray imaging as well as the same distance between the respective point source—detector-pairs 21, 23, and 26, 27, respectively. The X-ray fan- or cone-beam 22 and the virtual fan- or cone-beam 28, therefore, have different angulations or orientations but the same shape and size. Therefore, the X-ray image 24 and the second final MR image 29 have the same geometric or distortion characteristics and may thus easily be compared without any further processing or scaling.

The position of the virtual point source 26 (e.g., the angulation for the virtual projection or the final MR image 29) may be predetermined. The position of the virtual point source 26 may, for example, be provided as an input for the system or for the MR device prior to the acquisition of the MR data set. The angulation for the virtual projection or the final MR image 29 may depend on individual requirements, conditions, or constraints on a case-by-case basis.

While the X-ray image 24 and the second final MR image 29 may not be meaningfully overlaid or superimposed upon each other, since the X-ray image 24 and the second final MR image 29 may show the imaged object from different perspectives, the X-ray image 24 and the second final MR image 29 may show the tumor 20 or, for example, a vascular system or a vascular bifurcations, from different viewing angles. This may provide a physician with spatial information necessary to safely and reliably perform a medical procedure, such as guiding a catheter or a medical instrument.

The described examples and embodiments illustrate how a fast simultaneous acquisition of X-ray and MR projection images with the same projection geometry may be performed, which enables a combined radiography and magnetic resonance imaging in real-time. Because only a limited portion of the k-space of the imaged object is sampled, the described method may significantly improve upon existing real-time imaging techniques and applications, such as fluoroscopy, due to the improved soft tissue detail provided by the MR imaging supplementing the high spatial resolution achievable with X-ray imaging.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for magnetic resonance imaging, the method comprising:

acquiring a magnetic resonance (MR) data set of a first portion of an object, the acquiring of the MR data set of the first portion of the object comprising sampling only a portion of a k-space of the object, wherein the sampled portion of the k-space is substantially formed as one triangle or two triangles symmetrically arranged around an X-axis of a coordinate system of the k-space, the X-axis representing spatial frequencies in an X-direction, each triangle of the two triangles having a respective tip located at a point of origin of the coordinate system of the k-space and each triangle of the two triangles extending along a Y-axis of the coordinate system of the k-space, the Y-axis representing spatial frequencies in a Y-direction, or wherein the sampled portion of the k-space is composed of multiple planes, each plane of the multiple planes extending through the point of origin of the coordinate system of the k-space and being tangential to a common spherical cap centered around or symmetrically arranged around the Y-axis of the coordinate system of the k-space;

applying an inverse Fourier transformation to the MR data set to transform the MR data set from the k-space to an image space; and computing a final MR image with a fan-beam geometry based on the transformed MR data set in the image space when the MR data set is acquired from the sampled portion of the k-space formed as the one triangle or the two triangles, or computing the final MR image with a cone-beam geometry based on the transformed MR data set in the image space when the MR data set is acquired from the sampled portion of the k-space composed of the multiple planes.

2. The method of claim 1, further comprising:

acquiring X-ray image data of a second portion of the object using a fan- or cone-beam geometry, wherein the first portion of the object and the second portion of the object at least partly overlap each other, wherein the final MR image is computed with a fan- or cone-beam geometry corresponding to the fan- or cone-beam geometry of the X-ray image data.

3. The method of claim 2, wherein the portion of the k-space is sampled using a Cartesian grid sampling scheme.

4. The method of claim 2, wherein the portion of the k-space is sampled using a sampling scheme with sampling points arranged on two lines crossing the portion of the k-space from one edge to another edge in opposing zig-zag schemes.

5. The method of claim 2, wherein the final MR image is generated using a same angle, a same orientation, or a same angle and same orientation for the corresponding fan- or cone-beam geometry as is used in acquiring the X-ray image data.

6. The method of claim 2, wherein the final MR image is generated using a different angle, a different orientation, or a different angle and a different orientation for the corresponding fan- or cone-beam geometry than for acquiring the X-ray image data.

7. The method of claim 2, wherein the X-ray image data and the MR data set are acquired substantially simultaneously.

8. The method of claim 7, wherein the X-ray image data and the MR data set are acquired within 200 milliseconds of each other.

9. The method of claim 2, wherein the X-ray image data and the final MR image are automatically superimposed upon each other.

10. The method of claim 1, wherein when the portion of the k-space is formed as the one triangle or the two triangles, the portion of the k-space is sampled along lines through the point of origin of the coordinate system of the k-space, and wherein the inverse Fourier transformation is applied separately to respective data for each line or plane, thereby generating an interim MR image with a parallel projection geometry for each line or plane.

11. The method of claim 1, wherein an interpolation of the MR data set in k-space or an interpolation of a Fourier transform is performed to generate interpolated data points, and wherein the inverse Fourier transformation is applied to the interpolated data points, or the final MR image is generated based on the interpolated data points, respectively.

12. A system for magnetic resonance imaging, the system comprising:

a magnetic resonance (MR) imaging device configured to acquire an MR data set of a first portion of an object, the acquisition of the MR data set comprising sampling of only a portion of a k-space of the object, wherein the sampled portion of the k-space is substantially formed as one triangle or two triangles symmetrically arranged around an X-axis of a coordinate system of the k-space, the X-axis representing spatial frequencies in an X-direction, each triangle of the two triangles having a respective tip located at a point of origin of the coordinate system of the k-space and each triangle of the two triangles extending along a Y-axis of the coordinate system of the k-space, the Y-axis representing spatial frequencies in a Y-direction, or wherein the sampled portion of the k-space is composed of multiple planes, each of the multiple planes extending through the point of origin of the coordinate system of the k-space and being tangential to a common spherical cap centered around or symmetrically arranged around the Y-axis of the coordinate system of the k-space; and a data processor configured to:

automatically apply an inverse Fourier transformation to the MR data set, such that the MR data set is transformed from the k-space to an image space; and automatically compute a final MR image with a fan-beam geometry based on the transformed MR data set in the image space when the MR data set is acquired from the sampled portion of the k-space formed as the one triangle or the two triangles, or automatically compute the final MR image with a cone-beam geometry based on the transformed MR data set in the image space when the MR data set is acquired from the sampled portion of the k-space composed of the multiple planes.

13. The system of claim 12, further comprising an X-ray device configured to acquire X-ray image data of a second portion of the object using a fan- or cone-beam geometry, wherein the first portion and the second portion at least partly overlap each other, wherein the data processor is further configured to automatically compute the final MR image with the fan- or cone-beam geometry corresponding to the fan- or cone-beam geometry of the X-ray image data.

14. The system of claim 13, wherein the X-ray device and the magnetic resonance imaging device are arranged so that isocenters of both devices spatially coincide.

* * * * *